United States Patent [19]
Goswami

[11] Patent Number: 5,933,702
[45] Date of Patent: *Aug. 3, 1999

[54] PHOTOCATALYTIC AIR DISINFECTION

[75] Inventor: D. Yogi Goswami, Gainesville, Fla.

[73] Assignee: Universal Air Technology, Lake Hopatcong, N.J.

[*] Notice: This patent is subject to a terminal disclaimer.

[21] Appl. No.: 08/988,814

[22] Filed: Dec. 11, 1997

Related U.S. Application Data

[60] Division of application No. 08/647,070, May 9, 1996, which is a continuation-in-part of application No. 08/524,284, Sep. 6, 1995, Pat. No. 5,835,840.

[51] Int. Cl.[6] ........................................... A61L 9/20
[52] U.S. Cl. ........................................ 422/186.3; 422/24
[58] Field of Search .................... 422/24, 186.3

[56] References Cited

U.S. PATENT DOCUMENTS

| | | |
|---|---|---|
| 2,265,252 | 12/1941 | Schaefer . |
| 2,628,083 | 2/1953 | Rense . |
| 2,638,644 | 5/1953 | Rauhut . |
| 3,973,927 | 8/1976 | Furchner et al. ............ 422/22 X |
| 4,102,654 | 7/1978 | Pellin . |
| 4,306,358 | 12/1981 | King, Jr. ............................ 34/487 |
| 4,437,954 | 3/1984 | Sammells et al. .......... 422/186 X |
| 4,464,336 | 8/1984 | Hiramoto . |
| 4,554,719 | 11/1985 | Lewis ...................... 29/890.039 |
| 4,694,179 | 9/1987 | Lew et al. .................... 422/24 X |

(List continued on next page.)

FOREIGN PATENT DOCUMENTS

| | | |
|---|---|---|
| B-76028/87 | 1/1988 | Australia . |
| 63-80833 | 4/1988 | Japan . |
| 2207824 | 8/1990 | Japan . |
| 3106420 | 5/1991 | Japan . |

OTHER PUBLICATIONS

Matthews, *Solar Energy*, 38(6), 405–13 (1987).
Trivedi, *Photocatalytic Disinfection of Airbourne Microorganisms* (Univ. of Florida, Sep. 6, 1994).
Sabate et al., *J. Catal.*, 127, 167–77 (1991).
Suzuki, "Photocatalytic Air Purification on $TiO_2$ Coated Honeycomb Support," *Photocat. Purification and Treat. of Water and Air* (Ollis and Al–Ekabi, Eds., Elsevier Sci. Pubs. 1993) 421–434.
Fujishima et al., "Biochemical Application of $TiO_2$ Photocatalysts," *Photocat. Purification and Treat. of Water and Air* (Ollis and Al–Ekabi Eds., Elsevier Sci. Pubs. 1993) 193–205.
Wang et al., "Control of VOC Emissions from Air–Stripping Towers: Development of Gas–Phase Photocatalytic Process," *Photocat. Purification and Treat. of Water and Air* (Ollis and Al–Ekabi, Eds., Elsevier Sci. Pubs. 1993) 733–739.
Anderson et al., "Photodegradation of trichloroethylene in the gas phase $TiO_2$ porous ceramic membrane," *Photocat. Purification and Treat. of Water and Air* (Ollis and Al–Ekabi, Eds., Elsevier Sci. Pubs. 1993) 405–420.
Wang et al., "Gas Phase Photocatalytic Process for the Control of VOC Emissions from Air–Stripping Towers," *Proc.–Annu. Conf., Am. Water Assoc.*, 585–605 (1993).

*Primary Examiner*—Daniel J. Jenkins
*Attorney, Agent, or Firm*—Lerner, David, Littenberg, Krumholz & Mentlik, LLP

[57] ABSTRACT

A method for disinfecting an air stream containing microorganisms including the steps of providing an air stream containing microorganisms having a relative humidity greater than about 40%; and contacting the air stream with a photocatalyst having a predetermined band gap energy in the presence of a source of photons having a wavelength corresponding to the band gap energy of the photocatalyst, so that at least a portion of the microorganisms in the air stream are destroyed by photocatalytic oxidation. Devices embodying the method of the invention are disclosed, such as stand-alone devices and devices incorporated into the HVAC systems of buildings, including the air supply registers. Photocatalyst-coated filter media capable of trapping bioaerosols are also disclosed.

91 Claims, 12 Drawing Sheets

U.S. PATENT DOCUMENTS

| | | | |
|---|---|---|---|
| 4,734,111 | 3/1988 | Hoffmann et al. | 435/266 |
| 4,750,917 | 6/1988 | Fujii | 422/24 X |
| 4,806,768 | 2/1989 | Keutenedjian . | |
| 4,859,594 | 8/1989 | Portier | 435/172.1 |
| 4,931,654 | 6/1990 | Horng . | |
| 4,955,208 | 9/1990 | Kawashima et al. | 422/122 X |
| 4,966,759 | 10/1990 | Robertson et al. | 422/186 |
| 4,990,311 | 2/1991 | Hirai et al. | 422/4 |
| 5,032,241 | 7/1991 | Robertson et al. | 204/157.15 |
| 5,045,288 | 9/1991 | Raupp et al. | 422/186.3 |
| 5,069,885 | 12/1991 | Ritchie | 422/186 |
| 5,151,252 | 9/1992 | Mass | 422/24 X |
| 5,186,907 | 2/1993 | Yanagi et al. | 422/186.3 |
| 5,200,156 | 4/1993 | Wedekamp | 422/24 X |
| 5,219,534 | 6/1993 | Reynolds | 422/186.3 |
| 5,225,167 | 7/1993 | Wetzel | 422/121 |
| 5,227,053 | 7/1993 | Bryan | 210/143 |
| 5,260,036 | 11/1993 | Weigold et al. | 422/186.3 |
| 5,262,066 | 11/1993 | Van Soye et al. | 422/24 X |
| 5,397,552 | 3/1995 | Weigold et al. . | |
| 5,413,768 | 5/1995 | Stanley, Jr. | 422/24 X |
| 5,433,763 | 7/1995 | Shagott et al. | 55/323 |
| 5,449,443 | 9/1995 | Jacoby et al. | 204/157.3 |
| 5,456,740 | 10/1995 | Snow et al. | 96/11 |
| 5,501,801 | 3/1996 | Zhang et al. . | |
| 5,554,300 | 9/1996 | Butters et al. . | |
| 5,589,132 | 12/1996 | Zippel . | |
| 5,604,339 | 2/1997 | Tabatabaie-Raissi et al. . | |

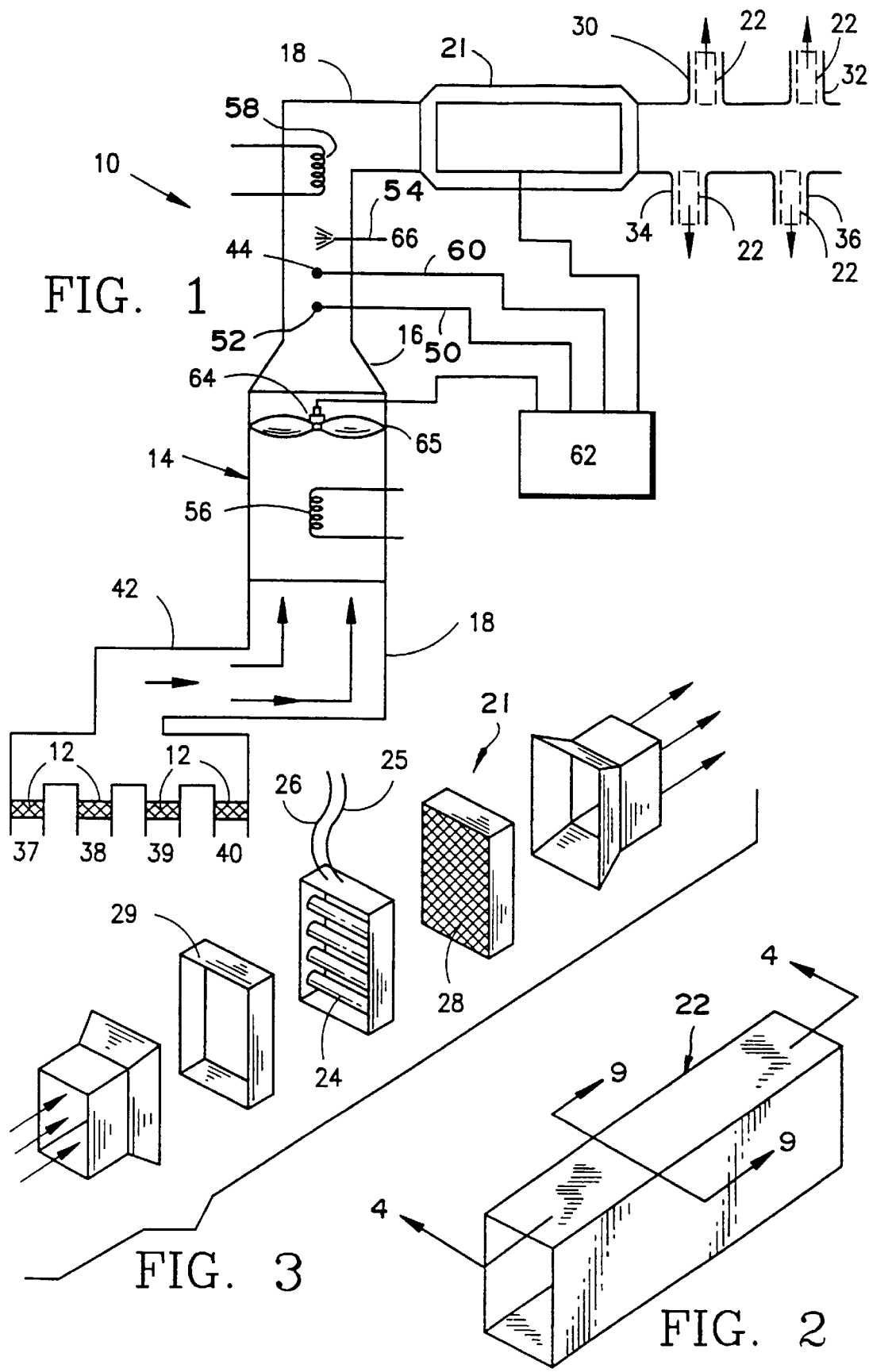

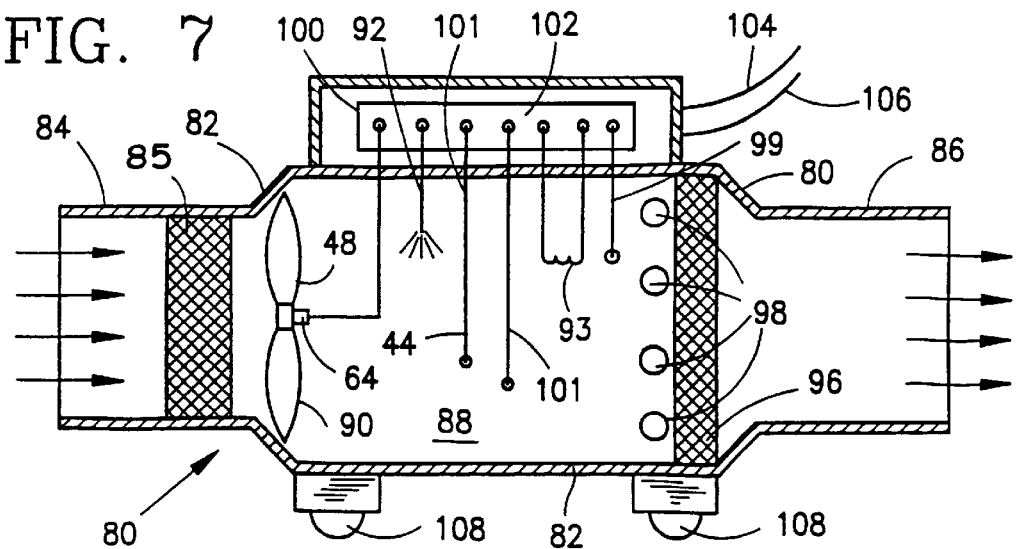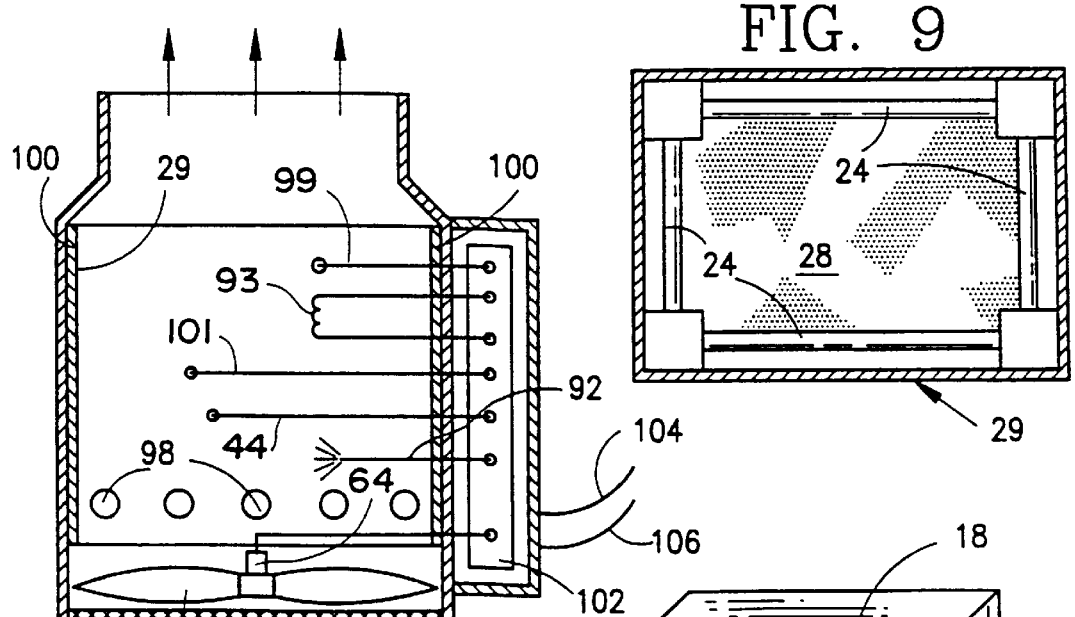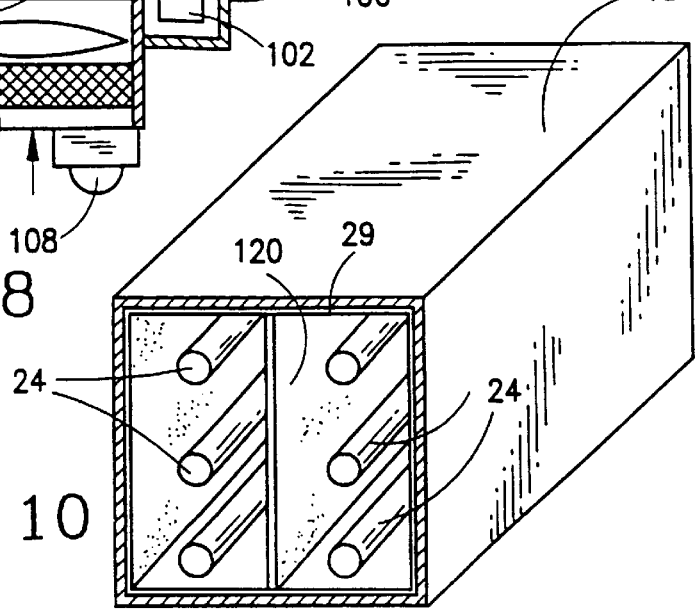

5,933,702

PHOTOCATALYTIC AIR DISINFECTION

CROSS REFERENCE TO RELATED APPLICATION

This is a divisional of U.S. application Ser. No. 08/647,070 filed May 9, 1996, which is a Continuation In Part application of U.S. patent application Ser. No. 08/524,284 now U.S. Pat. No. 5,835,840 by D. Yogi Goswami entitled, "Photocatalytic System for Air Quality" received by the United States Patent and Trademark Office on Sep. 6, 1995, the disclosure of which is incorporated herein by reference.

BACKGROUND OF THE INVENTION

The present invention relates to methods for air disinfection by photocatalytic oxidation, and, in particular, to methods in which the air to be disinfected is provided at a relative humidity greater than about 40%, and then contacted with a photocatalyst in the presence of ultraviolet (UV) light so that at least a portion of any microorganisms in the air are destroyed by photocatalytic oxidation. The present invention also relates to air disinfection devices having a photocatalyst-coated surface illuminated by a UV light source and having means for contacting air with the photocatalyst-coated surface and means for maintaining the relative humidity of the air above about 40%, so that microorganisms in the air are destroyed by photocatalytic oxidation when the photocatalyst-coated surface is illuminated with UV light.

Americans spend 90% of their time indoors, and while indoors, are exposed to a variety of airborne contaminants such as volatile organic compounds (VOC's), radon and biological organisms. In a 1980 study, the Environmental Protective Agency (EPA) concluded that indoor air pollution posed a greater health risk than outdoor air pollution. Indoor air contamination is estimated to cause significant increases in medical costs and a decline in work productivity.

In building circulating systems, pollutant levels from individual sources may not pose a significant risk by themselves. However, many buildings have more than one source that contributes to indoor air pollution. Illnesses resulting from such indoor pollutants are sometimes known as the "sick building syndrome." The causes of indoor air pollution are unwanted particulate matter, unwanted chemical substances and microbial contaminants. In the first two cases, conventional technology can oftentimes provide a solution by filtration and adequate ventilation. The problem of volatile organic compounds (VOCs) and microbiological contamination creates a more serious obstacle.

Because so many Americans spend a great deal of time in offices and buildings with mechanical heating, cooling, and ventilating systems, such systems pose a risk of biological contamination. In recent years, biological problems in indoor environments have received considerable attention. The Legionnaires' disease outbreak in Philadelphia in 1976 is probably the most publicized case of illness caused by indoor pollutants.

Biological contamination includes bacteria, molds, and viruses. A contaminated central air system can become a breeding ground for biological contaminants and the forced air can distribute the contaminants throughout the building.

During the past three to four decades, significant changes have occurred in the construction and operation of buildings. The building envelope has become tighter, thus less outside air is being used in heating, ventilation and air conditioning (HVAC) systems. Microbial agents are not so readily diluted by mixing with fresh air. Energy conservation programs have resulted in buildings with moisture in the indoor environment, and that has facilitated the growth of certain types of microorganisms.

Because of neglected maintenance programs in some buildings, excessive dirt, a nutrient for microorganisms, accumulates in niches of the HVAC systems. This results in maladies referred to as building related illness, building sickness and sick building syndrome.

Several microbiological particle control techniques exist (including mechanical and electrostatic filters) that may be used as part of the building's forced air heating/cooling system to reduce indoor concentrations of respirable particles. Microbiological filters have been used for disinfection of air and other gases because of their low cost and ease of handling. These filters can be constructed to remove not only microorganisms but submicron particles as well. For efficient and economic operation of these filters, the aerosol content of the air to be filtered must be low. (Microorganisms, particles, or droplets of liquid dispersed in air are referred to as aerosols.) A disadvantage of such filters is that they do not permanently remove the contaminants, but just transfer them to another medium; that is, the filter. Clogging will cause high pressure drops in the duct.

One viable solution is to permanently remove the contaminant and produce nontoxic residue. UV disinfection has been widely used in the past to destroy biological contaminants and toxic chemicals.

Such UV treatment has worked well for disinfection but the indoor environment may also be contaminated with low level toxic chemicals such as formaldehyde, styrene, and toluene. Ultraviolet energy alone has proven ineffective in degrading these chemicals. For instance, U.S. Pat. No. 5,045,288 to Raupp and Dibble, and U.S. Pat. Nos. 4,892,712; 4,966,759; and 5,032,241 to Robertson and Henderson use UV to treat fluids and gases that contain pollutants.

One alternative that has gained much attention is photocatalytic oxidation, which involves the use of a photocatalyst such as $TiO_2$ for the total destruction of hydrocarbons and microorganisms in water. Patel, *Antibacterial Effect Of Catalyzed Radiation,* Masters Thesis, University of Florida, Gainesville (1993) reports powdered $TiO_2$ to be capable of killing *Serratia marcescens* after irradiation for 60–120 minutes in water. Saito et al., *J. Photochem. Photobiol. B:Biol.,* 14, 369–79 (1992); Matsunaga, *J. Antibact. Antifungic. Agents,* 13, 211–20 (1985); Nagane et al., *J. Dent. Res.,* 68, 1696–7 (1989) and Moriaka et al., *Caries. Res.,* 22, 230–1 (1988), report $TiO_2$ to be capable of killing *E. coli* and *Lactobacillus acidophilus* after aeration for 60–120 minutes in water. Wang et al., *Proceedings of the First International Conference on $TiO_2$ Photocatalytic Purification and Treatment of Water and Air* (London, Ontario, Canada, Nov. 8–13, 1992) pp. 733–9; Wang et al., *Proc. AWWA Conf.* (San Antonio, Tex., 1993); Savat et al., *J. Catalysis,* 127, 167–77 (1991) and Anderson et al., *Further Catalytic Purification of Water and Air,* 1, 405–20 (1993) report the gas phase detoxification of trichloroethylene (TCE) and other organic contaminants. There remains a need for a method by which microorganisms may be removed from the air.

SUMMARY OF THE INVENTION

This need is met by the present invention.

It has now been discovered that air may be disinfected of microorganisms by the photocatalytic oxidation stimulated by the action of UV light on a photocatalyst under controlled humidity conditions.

A primary objective of this invention is to provide a viable solution for indoor air purification and detoxification that can be used with new or already installed air duct systems.

Another objective of this invention is to provide a relatively inexpensive detoxification reactor which can be placed within the duct system of a troubled building. The reactor units can be disposed within one or several trunk ducts of the air distribution system or a reactor can be disposed in each duct leading to a room register.

A further objective of the invention is to provide a detoxification reactor unit which can be readily disposed in new circulation systems or as a modification to troubled circulation systems, or as a stand-alone air filtration unit, or as an exit ventilation system or it can be used as an exit chamber for a vacuum cleaning system.

A still further objective of the invention is to provide a means by which the airflow rate through the reactor and the humidity of that airflow can be regulated so as to produce the maximum destruction efficiency of a UV light acting on a catalyst such as $TiO_2$.

Another important objective of the invention is to provide a photocatalytic oxidation system that not only destroys microorganisms but also decontaminates the organic chemicals, as well as odors resulting from microorganisms and volatile organic contaminants which are often times found in indoor air.

Another objective of this invention is to provide a duct coated with the catalyst that will remain free of microorganisms if a light of appropriate wavelength range is incident on the catalyst coated duct surface.

A further objective of this invention is to provide stand-alone embodiments for purifying contaminated air departing from enclosures in which certain deleterious processes take place; for example, painting enclosures.

The stand-alone embodiment, in particular, also can be utilized in hospitals, including operating room where sterility of the air is critical, doctor waiting rooms, rest rooms and in other locations where recirculation is feasible and odor-reduction and a high degree of purification are necessary to provide comfort to those using these facilities.

Therefore, in accordance with one embodiment of the present invention, a method for disinfecting an air stream containing microorganisms includes the steps of providing an air stream containing microorganisms having a relative humidity greater than about 40%; and contacting the air stream with a photocatalyst having a predetermined band gap energy in the presence of a source of photons having a wavelength corresponding to the band gap energy of the photocatalyst, so that at least a portion of the microorganisms in the air stream are destroyed by photocatalytic oxidation. Preferred methods in accordance with the present invention also control the flow rate of the air stream so that at least a portion of the microorganisms in the air stream are destroyed.

The present invention also includes devices embodying the inventive method. Thus, in accordance with another embodiment of the present invention, a device for disinfecting a quantity of air containing microorganisms is provided having a surface coated with a photocatalyst having a predetermined band gap energy; means for illuminating the photocatalyst-coated surface with a source of photons having a wavelength corresponding to the band gap energy of the photocatalyst; means for contacting the air with the photocatalyst-coated surface, and means for maintaining the relative humidity of the air above about 40%, so that at least a portion of the microorganisms in the air are destroyed by photocatalytic oxidation upon contact with the photocatalyst when the photocatalyst-coated surface is illuminated with the UV light.

The methods and devices of the present invention are adapted for use within HVAC systems of buildings or as stand-alone units. Thus, according to one aspect of this embodiment of the present invention, a device is provided for disinfecting air containing microorganisms having a duct through which the air is moved; a blower connected to the duct to move the air therethrough; a photocatalyst having a predetermined band gap energy disposed in the duct; a lamp disposed in sufficient proximity to the photocatalyst to illuminate the photocatalyst with a source of photons having a wavelength corresponding to the band gap energy of the photocatalyst; and a humidity controller adapted to maintain the relative humidity of the air in the duct above about 40%, so that at least a portion of the microorganisms in the air are destroyed by photocatalytic oxidation upon contact with the photocatalyst when the photocatalyst is illuminated with the UV light from the lamp.

According to yet another aspect of this embodiment of the invention, a stand-alone device for disinfecting air containing microorganisms is provided having a chamber through which the air is moved; a blower connected to the chamber to move the air therethrough; a photocatalyst having a predetermined band gap energy disposed in the chamber; a lamp positioned to illuminate the photocatalyst with a source of photons having a wavelength corresponding to the band gap energy of the photocatalyst; and a humidity controller adapted to maintain the relative humidity of the air in the chamber above about 40%, so that at least a portion of the microorganisms in the air are destroyed by photocatalytic oxidation upon contact with the photocatalyst when the photocatalyst is illuminated with UV light.

The present invention also incorporates the discovery that the useful life of filter media capable of trapping bioaerosols containing microorganisms may be extended by coating the filter media with a photocatalyst having a predetermined band gap energy. When the filter media is illuminated with a source of photons having a wavelength corresponding to the band gap energy of the photocatalyst under conditions of relative humidity effective to initiate the aforementioned photocatalytic oxidation, at least a portion of the microorganisms entrapped by the filter media are destroyed, thereby purging the filter media of the entrapped bioaerosols, so that continued entrapment of bioaerosols by the filter media is possible, increasing the time period between the filter changes.

According to this embodiment of the present invention, a filter medium is provided capable of trapping bioaerosols having an upstream surface to be contacted with an air stream containing microorganisms, wherein the upstream surface of the filter medium is coated with a photocatalyst. Preferably, the filter medium is contained within a HEPA filter or a microporous filter.

The above and other objects, features and advantages of the present invention will become clear from the following description of the preferred embodiments considered in conjunction with the accompanying drawings.

BRIEF DESCRIPTION OF THE DRAWINGS

FIG. 1 is a diagrammatic-schematic of a typical heating/cooling duct system for a building with a reactor system of this invention incorporated therein;

FIG. 2 is a diagrammatic perspective view of a reactor unit for purposes of illustrating the cross-sections of other views;

FIG. 3 is an exploded diagrammatic view illustrating several of principal components of the reactor unit;

FIG. 7 is a longitudinal cross-sectional view of a stand-alone embodiment;

FIG. 8 is a vertical variation of the stand-alone unit of FIG. 7;

FIG. 9 is a cross-section along the line 9—9 showing the UV lamps disposed about the perimeter of a duct;

FIG. 10 is a diagrammatic perspective view illustrating the positioning of the UV lamps with respect to a catalytic insert;

Figure 4:
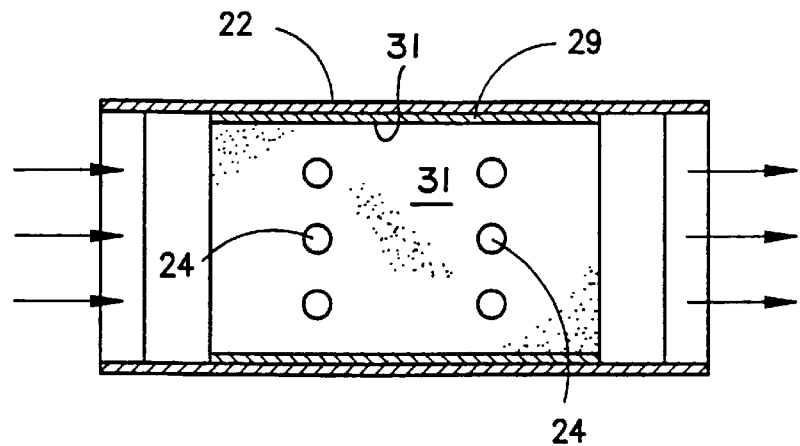
FIGS. 4, 5 and 6 are longitudinal cross-sections of various embodiments of the reactor unit along the line 4—4 of FIG. 2 showing the arrangement of UV lamps with respect to coated members.

It should be noted that the drawings are not necessarily to scale, but that certain elements have been expanded to show more clearly the various aspects of the present invention and their advantages.

DESCRIPTION OF THE PREFERRED EMBODIMENT

Referring now to the drawings wherein like elements are indicated by like numerals, an apparatus in accordance with the present invention embodying the method of the present invention is shown in FIG. 1 in which the numeral 10 depicts the system of this invention. In most buildings, a blower/fan causes the air from the various zones of an air conditioned space to be drawn into a duct system via inlet openings and particle/aerosol filters 12. The air then can pass over the heating coil of the furnace or the heating/cooling coil of an air conditioner/heat pump of the air conditioning unit 14. The cooling coil will act as a dehumidifier since it condenses moisture from air as it cools the air.

The fan 65 of the air handling unit 14 will force the air passing over the coils 13 and 15, into a duct system 18. In FIG. 1 there is a master reactor 21 along the duct 18. In many installations this will be sufficient. However, in the embodiment of FIG. 1, there is also shown a series of reactor units 22 disposed in branch lines of duct system 18.

FIG. 2 diagrammatically illustrates the major components within reactor 21. These components will also be found in reactors 22. These major components are a catalyst-coated liner 29, a bank of UV lamps 24 and a catalyst-coated mesh or matrix of surfaces 28. In some instances only a coated liner or a coated mesh is used. Here both are used. For purposes of the present invention, the catalyst-coated liner and mesh are referred to collectively as catalytic inserts. The lamps preferably deliver low energy photons of the UV-A and lower energy portion of the UV-B spectrum. A UV wavelength between about 300 and about 400 nm is preferred.

Figure 5:
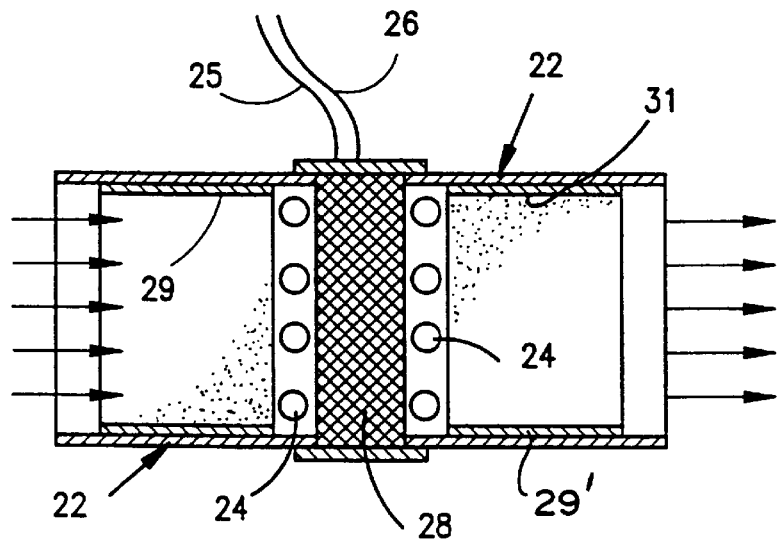
Figure 6:
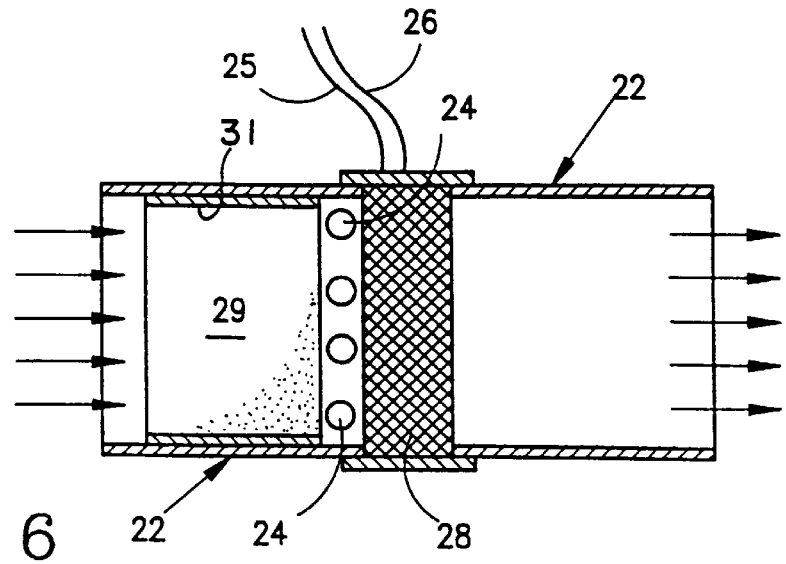

Various interiors of reactor 22 can be seen in FIGS. 4, 5 and 6. A bank of UV lamps 24, connected to an electrical source by way of electrical leads 25 and 26 are available to each reactor. The leads 25 and 26 are shown in FIGS. 5 and 6 but similar leads will be present in all embodiments. The UV rays from lamps 24, in these embodiments, strike a coated liner 29 (FIG. 4) or one side of a mesh and a coated liner 29 (FIG. 6) either or both of which may be coated with the photocatalyst. The UV rays may alternatively be directed to both sides of coated mesh 28 and coated liner sections 29 and 29' on each side thereof. See FIG. 5.

Essentially any material capable of catalyzing photocatalytic oxidation when illuminated with a source of photons in the presence of air having a relative humidity greater than about 40% is suitable for use as a photocatalyst in the present invention. Such materials are readily identified by those of ordinary skill in the art without undue experimentation. Examples of suitable photocatalysts are semiconductor materials such as $ZnO_2$, $TiO_2$, and the like; however, essentially any semiconductor material or a semiconductor in combination with a noble metal or other metal such as silver may be employed. Preferably, the photocatalyst is used in combination with a source of photons including wavelengths corresponding to the band gap energy of the photocatalyst. A preferred source of photons is UV light. The preferred photocatalyst is $TiO_2$, which has a band gap energy falling within the energy range of UV photons of wavelengths 300–400 nm.

The mesh 28 may be made out of any material to which a photocatalyst will adhere by conventional methods. The duct liners 29 may be made of any material that will allow the deposition and adherence of a photocatalyst on its interior surface 31 by conventional methods.

Some examples of such fibers and materials for the mesh include natural fibers such as cotton and wool, man-made and synthetic fibers such as rayon, polyester, polypropylene and Teflon, and other materials such as flame resistant fibrous materials and carbons and all other functional fibrous materials. The mesh 28 is constructed in a loose woven, non-woven or knitted configuration, or a combination thereof, such that it allows relative free flow of air without an excessive pressure drop.

After passing through the reactors 22 and departing the branch conduits 30, 32, 34 and 36, the air is directed to room registers. Obviously, in a large building there may be several dozen conduits of the 30–36 type branching from a plurality of main ducts. Each room normally has an air return opening. The air is returned from each room and recirculated through the system via a series of ducts depicted by the numerals 37, 38, 39 and 40. These ducts contain the filters 12 and merge into a collector duct 42 which returns the air to the intake side of he air conditioning unit 14 where it may be re-cooled or reheated and returned to the duct system 18.

The retention time of the circulating air in the reactor 21 over the catalyst-coated mesh 28 or the coated duct liner 29 is important. The speed of the air within the duct system is measured by way of a detector 44.

In FIG. 1 a conventional flow or speed detector 44 (a Mamac Anubar flow detector) is located in the main duct system 18. Speed detectors are oftentimes placed within each reactor 22 and it is that type of reactor which is described with respect to the stand-alone units described hereinafter.

The faster the air speed, the less time air will be retained over the catalytic surfaces of mesh 28 or in contact with the coated surfaces 31 of liner 29. As speed or volumetric displacement is lowered, retention time increases. As stated previously, it is usually desirable to maintain air movement throughout the building at all times. Here, air speed is adjusted for a maximum destruction of the deleterious matter by controlling the retention time over the catalytic surface.

This retention time will vary depending on the air flow rate, the size of the ducts, the area of the catalytic surface and other physical characteristics. In any event, the air speed or volume flow rate is entered into a microprocessor 62 from the detector 44. The microprocessor 62 in turn will control the speed of fan motor 64 and thus the air displacement of fan 65. The blower speed is always adjusted to provide the required residence time. For example, an air speed of approximately 70 ft/min over 2 inches thick catalytic mesh provided good disinfection and destruction rates in the experiments conducted.

Figure 14:
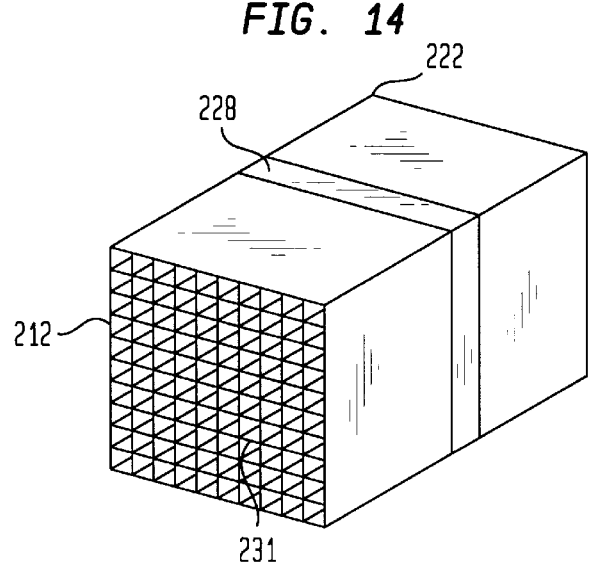
FIG. 14 is diagrammatic perspective view of another embodiment of a reactor unit in accordance with the present invention.
Figure 15:
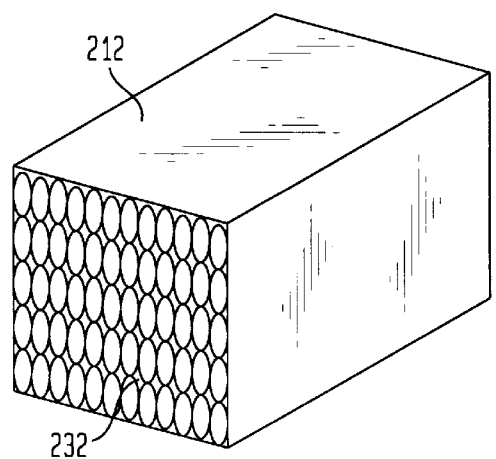
FIG. 15 is a diagrammatic perspective view of a catalytic insert in accordance with the present invention.
Figure 16:
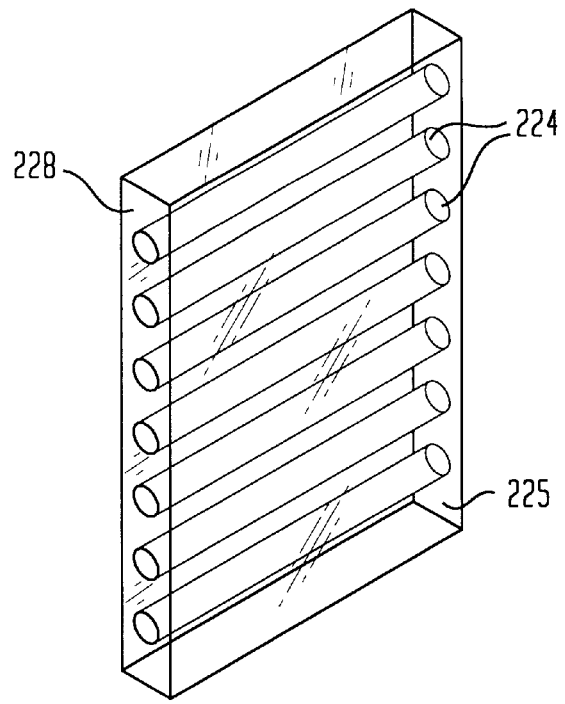
FIG. 16 is a diagrammatic perspective view of a UV lamp assembly in accordance with the present invention.
Figure 17:
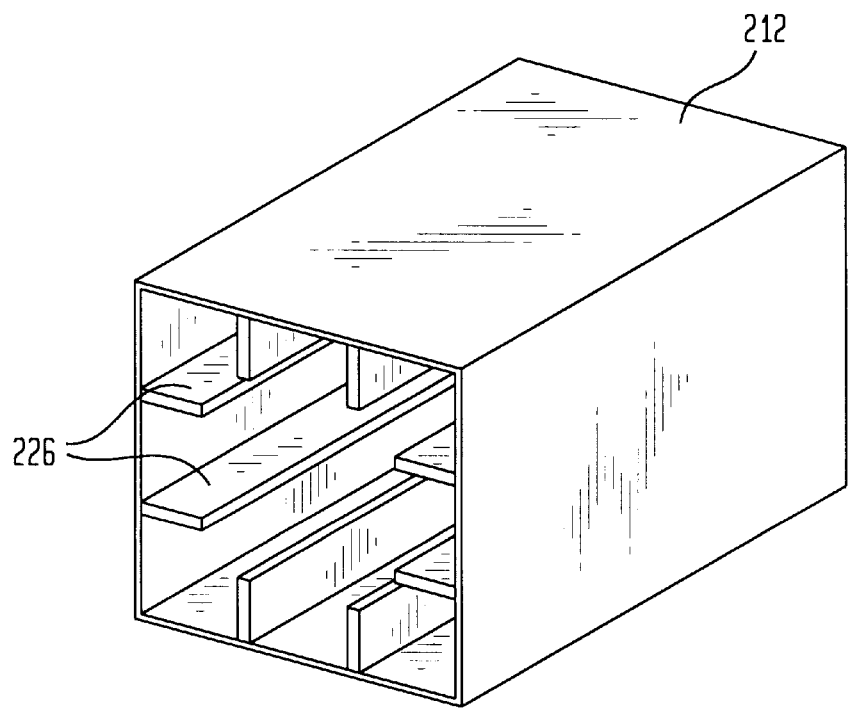
FIG. 17 is a diagrammatic perspective view of another embodiment of a catalytic insert in accordance with the present invention.

FIG. 14 shows a catalytic insert with a honeycomb structure having square air passages. FIG. 15 shows a catalytic insert construction with circular or oval inner passages. Other geometric shapes may be substituted for the ones shown in FIGS. 14 and 15. The photocatalyst-coated surface area within a catalytic insert may be increased through the addition of photocatalyst-coated fins 226, as shown in FIG. 17. A pleated surface may also be employed. The catalytic insert structures may be made of plastic, fiber, metal and other materials. The surface area of the mesh or the liner will depend on the expected concentrations of the contaminants and can be determined empirically for the installation involved without undue experimentation.

The relative humidity of the circulating air is also important. The relative humidity level of the air is critical for the destruction of microorganisms and must be at a level effective to enhance the destruction of at least a portion of the microorganisms by photocatalytic oxidation upon contact of the microorganisms with the photocatalyst when the photocatalyst is illuminated with UV light, that is, a relative humidity greater than about 40%. A relative humidity within the range between about 40% and about 70% is preferred, with a relative humidity between about 50% and about 60% being more preferred. A relative humidity of about 50% is most preferred.

Referring to FIG. 1, disposed along the length of duct 18 is a humidifier/dehumidifier unit 50 (sold by Sun Chemical as Model SUN 13) controlled by a detector probe of the type sold by Mamac as Model HV-2222. If detector 52 detects that the relative humidity in the air is less than 50%, a water spray or atomizer unit 54 is caused to spray enough moisture into the air stream as a fine mist to raise the relative humidity to approximately 50%. If the relative humidity is over 70%, moisture is removed by dehumidifier system here represented by cooling coil 56. Coil 56 can be a separate unit but in many instances, the coils of unit 14 can be utilized. A separate back-up coil 58 can also be provided. Dehumidification of air may be achieved by condensation of water using a cooling coil as shown in FIG. 1, or by other conventional techniques such as desiccant dehumidification.

The relative humidity and flow rate are preferably selected so that complete destruction of the microorganisms in the air stream is achieved. In our experiments, a relative humidity of 50% provided complete destruction of the microorganisms present with an air speed of approximately 70 ft/min over 2 inch thick catalytic mesh in a recirculating air duct. For purposes of the present invention, destroyed microorganisms are defined as microorganisms that have been completely killed, and does not include microorganisms that have been merely stunned, shocked or otherwise inactivated that are capable of being revived.

FIG. 1 discloses a master reactor 21 and branch reactors 22. In relatively small installations, only reactor 21 will be used. In relatively large installations only reactors 22 will be used. They are combined in FIG. 1 to show that the combination can also be employed.

The reactors may be provided with their own independent relative humidity and flow rate controls, so that each reactor functions as an independent photocatalytic device. Alternatively, each reactor may be adapted to the relative humidity and flow rate controls of the HVAC system in which it is installed, thereby converting the HVAC system into an apparatus in accordance with the present invention. Under such circumstances, the reactor will consist essentially of a catalytic insert and a UV light source for illuminating the surface. Such devices preferably have a photocatalyst coating surface area adapted to provide sufficient contact with the circulating air at the relative humidity and air flow rate of the HVAC system to destroy at least a portion of the microorganisms contained in the air.

FIGS. 4, 5 and 6 disclose various embodiments of lamp and catalyst location within an individual reactor 22. The UV lamps 24 are shown diagrammatically. The lamps are supported in any conventional fashion so that UV rays are directed on their respective catalytic surfaces.

FIG. 4 shows a reactor 22 in which rectangular liner catalytic insert 29 is disposed within a duct section. Its inner surface is coated with $TiO_2$ as indicated by the numeral 31.

FIG. 5 discloses a reactor 22 in which the catalytic inserts are coated liners 29 and 29', which are within the duct; and a bank or banks of UV lights 24 are disposed interiorally thereof on opposite sides of a filter/mesh 28. The UV lights 24 are shown crosswise of the duct.

Where appropriate, the filter/mesh 28 of reactor 22 may be a filter medium capable of trapping bioaerosols. Such a filter medium is preferably employed in any system in which it will allow a sufficient flow of air without an excessive pressure drop. Filters capable of trapping bioaerosols include HEPA filters, electrostatic filters and microporous filters. By coating the surface of the filter medium upstream of the air flow with a photocatalyst, illumination of the photocatalyst with UV light under conditions of relative humidity effective to produce photocatalytic oxidation will destroy at least a portion of the microorganisms in the bioaerosols trapped in the filter. This purges the filter medium of entrapped materials, thereby extending the useful light of the filter.

FIG. 6 discloses a reactor 22 in which a series of elongated UV lamps 24 are positioned crosswise of the duct and adjacent to a filter medium catalytic insert 28.

FIG. 9 is a reactor cross-section showing perimeter disposed UV lamps 24 within the liner 29 of the catalytic insert and adjacent to the filter 28.

The present invention also contemplates a method in which the photocatalyst-coated surface is provided in a duct section by painting the interior duct walls with the photocatalyst coating. UV lamps are then installed in the duct to illuminate the photocatalyst-coated interior duct walls.

Figure 18:
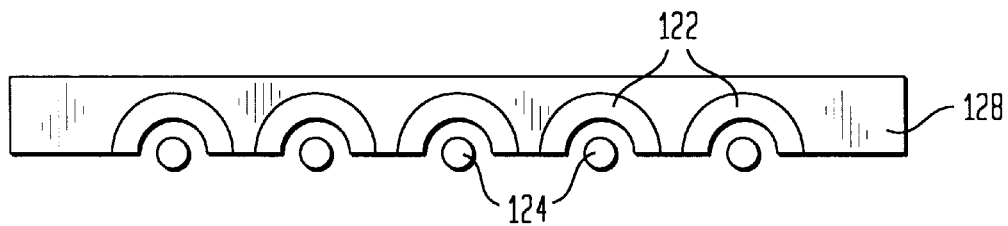
FIG. 18 is a longitudinal cross-sectional view of a wall-mounted UV lamp assembly.
Figure 19:
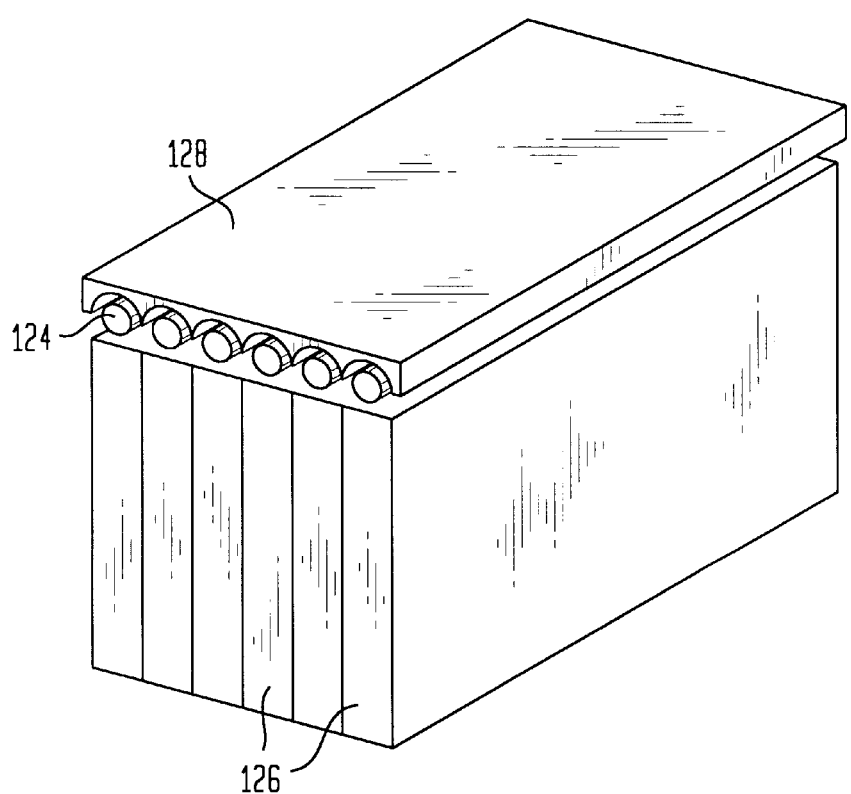
FIG. 19 is a diagrammatic perspective view of a reactor unit employing the wall-mounted UV lamp assembly depicted in FIG. 18.

The UV lamp assemblies for illuminating catalytic inserts may be mounted on duct walls. FIG. 18 depicts a wall mounted lamp assembly 128 with aluminized reflectors 122 reflecting UV light from lamps 124. FIG. 19 depicts the relationship between the wall-mounted assembly 120 and photocatalyst-coated inserts 126.

Figure 22:
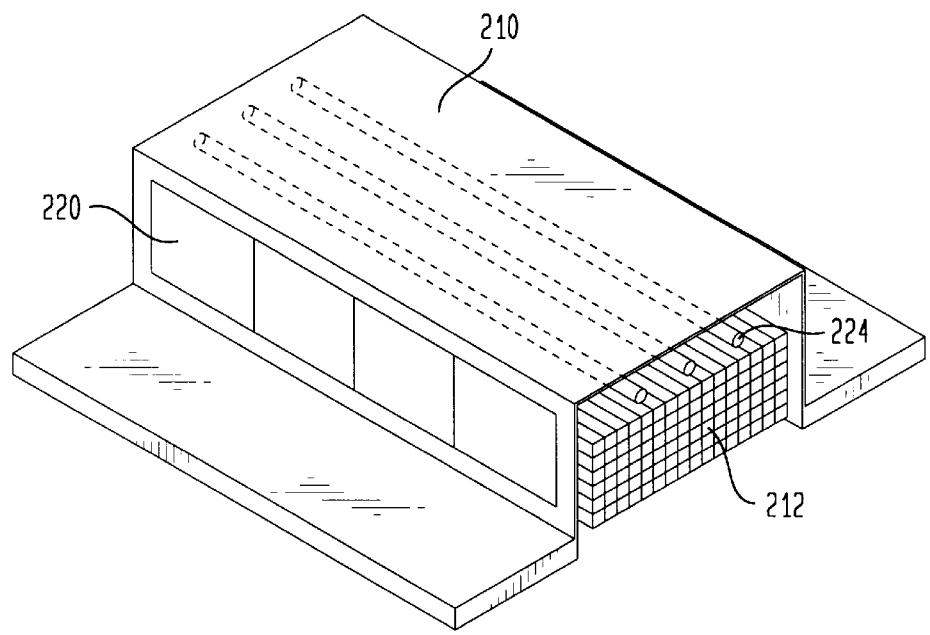
FIGS. 22 and 23 are diagrammatic perspective views of reactor embodiments of the present invention mounted in the air supply registers of HVAC systems.
Figure 23:
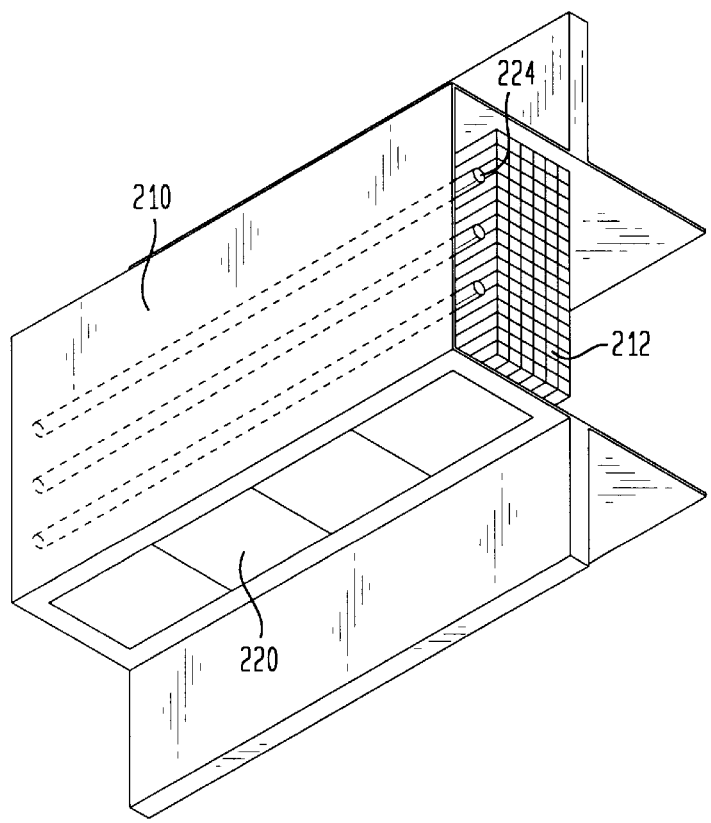
Figure 24:
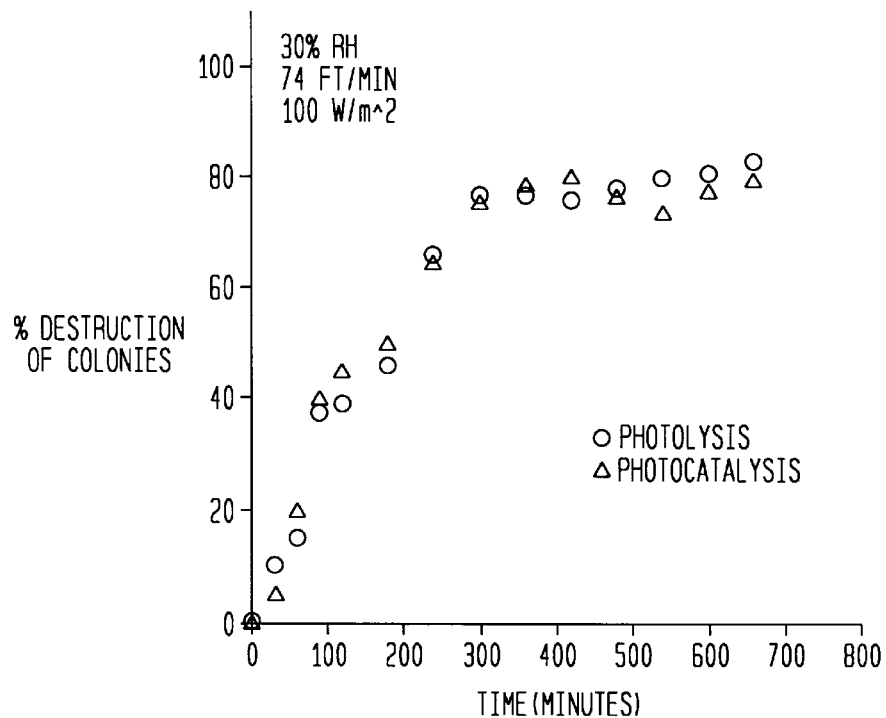
FIG. 24 depicts the destruction of *Serratia marcescens* by photolysis and photocatalysis at 30% RH.
Figure 25:
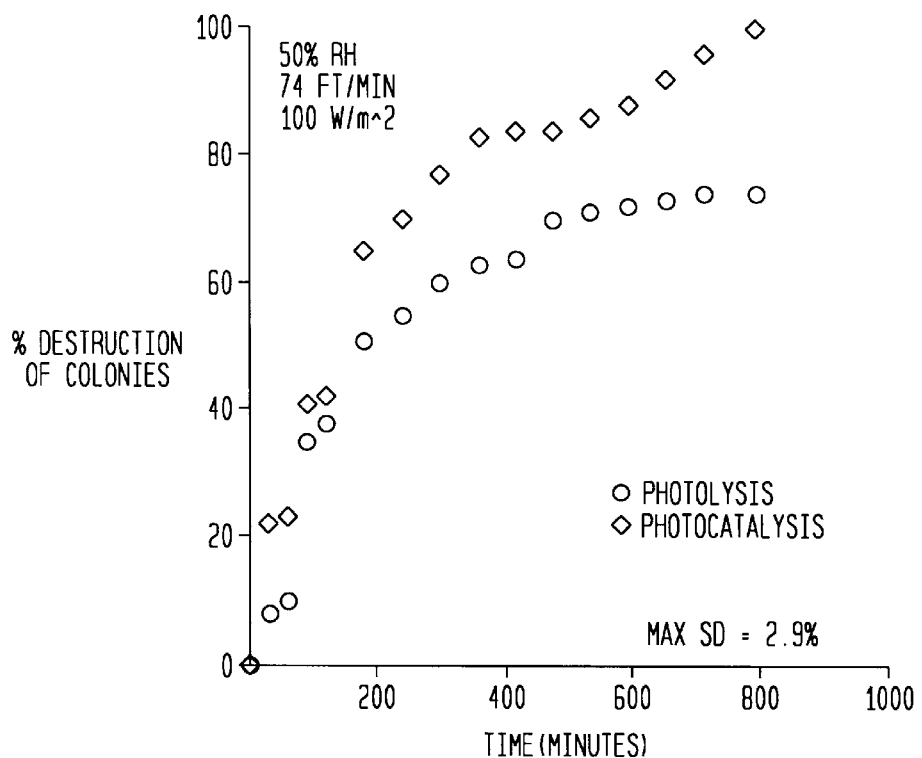
FIG. 25 depicts the destruction of *Serratia marcescens* by photolysis and photocatalysis at 50% RH.
Figure 26:
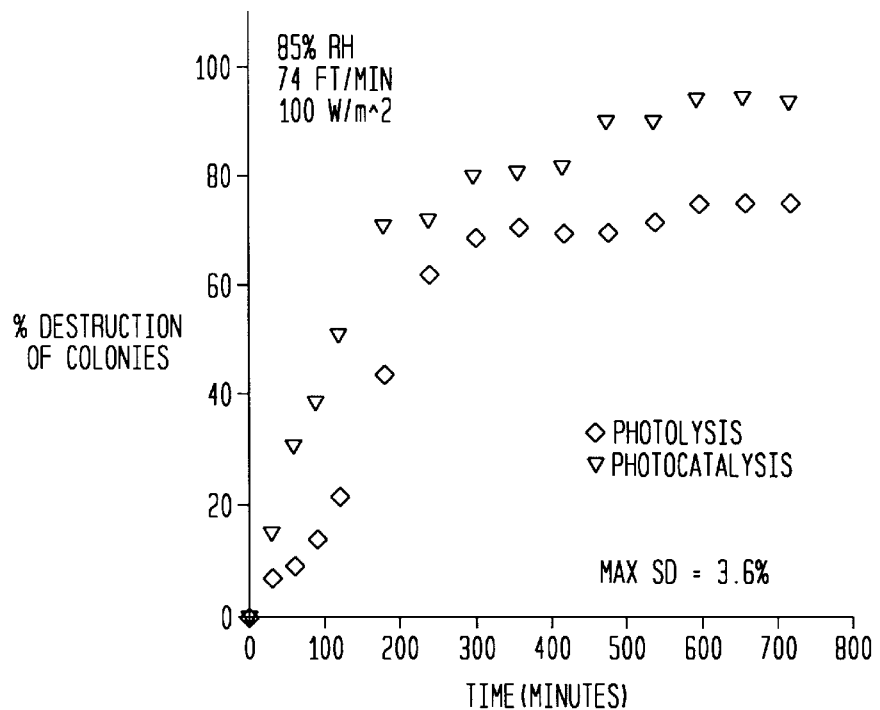
FIG. 26 depicts the destruction of *Serratia marcescens* by photolysis and photocatalysis at 85% RH.
Figure 27:
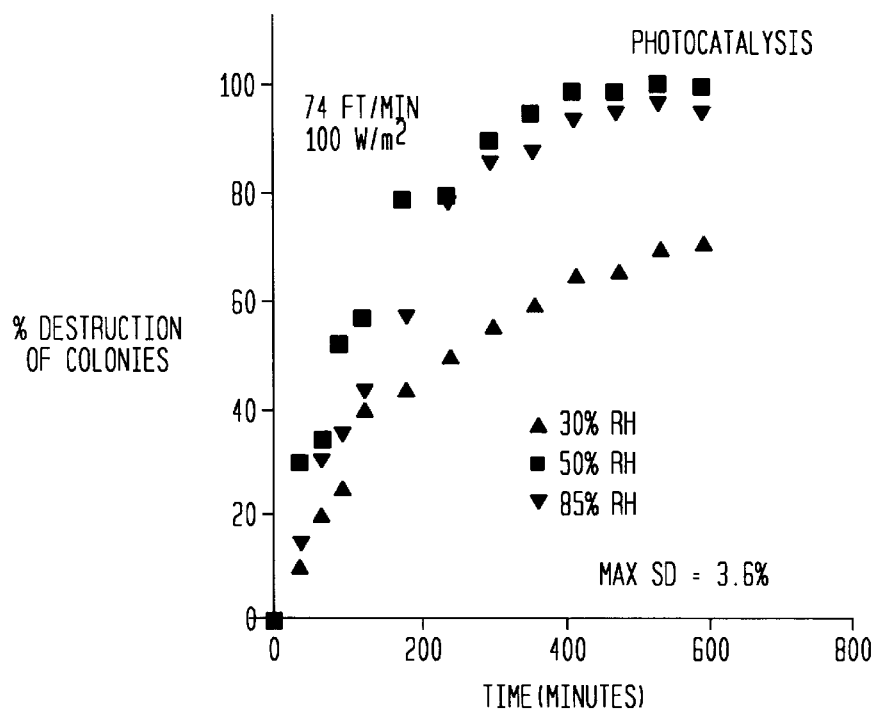
FIG. 27 depicts the effect of different humidities on destruction of *Serratia marcescens*.
Figure 28:
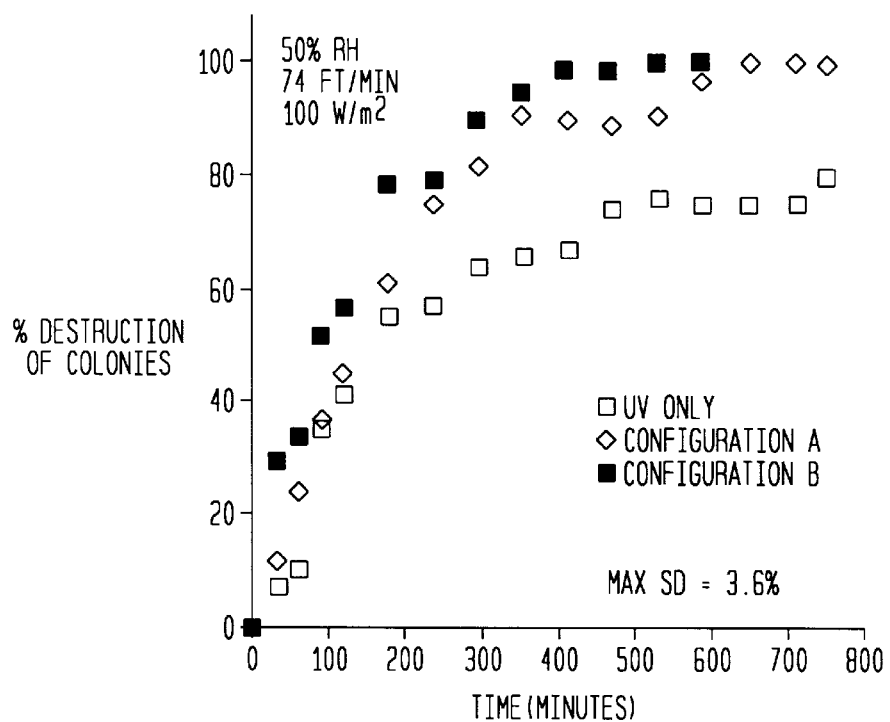
FIG. 28 depicts the destruction of *Serratia marcescens* by photolysis and by photocatalysis with two different reactor configurations at 50% RH and a UV intensity of 100 W/m$^2$.
Figure 29:
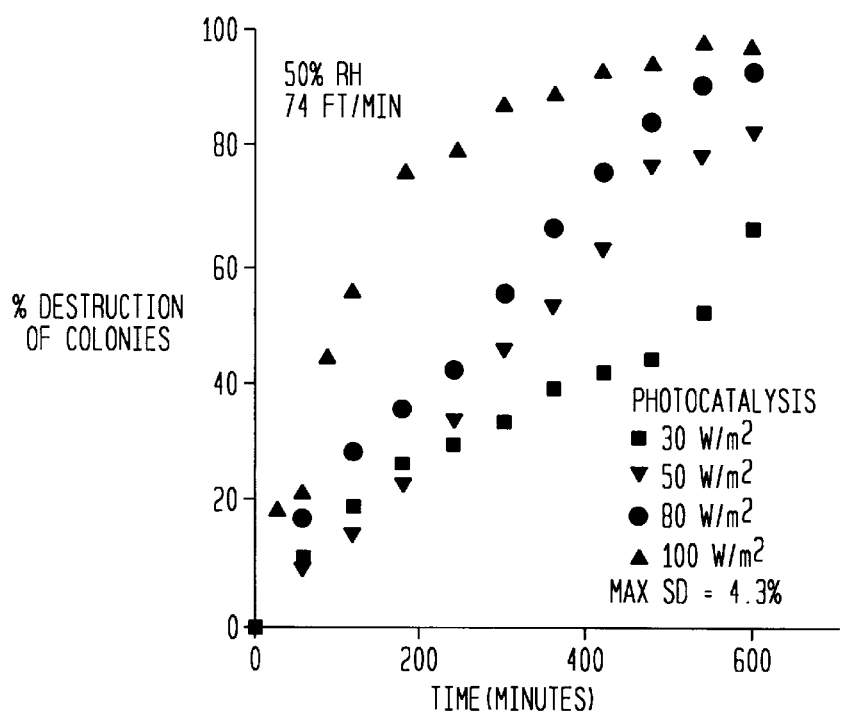
FIG. 29 depicts the destruction of *Serratia marcescens* at different UV intensities.

The reactors may also be installed in air supply registers of HVAC systems. FIGS. 22 and 23 show details of units adapted for such installation. As the air comes out of the HVAC duct, instead of going directly into the room, it is first treated by the photocatalytic disinfection method of the present invention by flowing through register 210. The unit essentially consists of a catalytic insert 212, UV light source 224 and air outlet 220. Single or multiple air outlets may be employed, depending upon the residence time required. The inside surface of the catalytic insert 212 is coated with a photocatalyst. UV lamps 224 are operated by battery or electrical power (not shown).

The UV lamps 224 and catalytic insert 212 of the register are removable. Any of the catalytic inserts depicted in the reactors of FIGS. 4–6 are suitable for use with the register 210.

The essentials of this invention can be utilized independently of a duct system. Such a stand-alone unit 80 is shown in FIG. 7. The unit 80 includes a housing 82 having an inlet 84 and an outlet 86. Intermediate the inlet and outlet is a chamber 88 that includes a control fan 90, a humidifier 92, a dehumidifier 93, a fan motor 64 for driving fan 48, and catalytic insert 96 upon which UV light is directed from a series of UV lamps 98. An air speed detector 99 determines the air flow displacement. A second chamber 100 is provided on the housing 82 to enclose a microprocessor 102. The electric power for the unit 80 is provided to the system through the control processor 102 via leads 104 and 106. The unit 80 may be operated without its own humidity control system if the proper humidity can be insured by an air conditioning system external to the unit 80. Alternatively, the stand-alone unit may be operated in tandem with a humidifier or dehumidifier without departing from the method or devices of the present invention. The stand-alone unit 80 may also be operated without the airspeed detector 99, if the unit 80 is designed and constructed with a constant air flow rate fan 48 matched with the cross sectional area of the housing 82 to provide the required residence time for the air flow over the catalyst.

The stand-alone unit 80 can be supported by wheels 108 so that it can be easily moved to a position within the room where it is most likely to encourage air flow circulation throughout the entire room. Also, the stand-alone unit can be utilized as an exhaust unit from a room in which undesirable fumes are present which one does not wish to exhaust into the atmosphere without treating them first. For instance, paint shops or in other industrial plants, the stand-alone unit 80 can be built into a roof or any exterior wall or it can be adapted for window support in the same fashion as a room air conditioner. In any event, contaminated air is cleansed before reaching the atmosphere.

Control and operation for the stand-alone unit is the same as that previously described. When power is supplied, the fan 48 will draw air into the inlet 84. A particulate prefilter 85 is provided to maintain the interior of the stand-alone unit free of dirt that might damage coated mesh 96 or a coated liner if one is used in combination with a mesh. The particulate prefilter can be HEPA type, electrostatic type, or any commercially available unit. Unlike units installed in the ducts of HVAC systems, particulate prefilters may be employed with stand-alone units because in such standalone units the pressure drop associated with a prefilter is acceptable. In the alternative, the prefilter may be omitted if the air is reasonably free of particulates. The UV lights 98 are illuminated at the same time the fan begins to rotate.

Detector 44 will measure air speed and the information is fed to microprocessor 102. The microprocessor will then adjust the rpm of the fan to ensure the proper residence time the air is subjected to the UV light while traversing the $TiO_2$-coated surfaces, whether a liner or a mesh.

While this is occurring, the humidity of the incoming air is monitored by unit 101 and that data is sent to the microprocessor. If the air has a humidity of below 40%, the wetting unit or humidifier 92 is actuated until a 50% relative humidity is obtained. If the air has a relative humidity of above 70%, the dehumidifier 93, here utilizing a heating coil 93, is actuated until the relative humidity is lowered to 50%.

FIG. 8 is a vertical embodiment of a stand-alone unit. Here a particulate/aerosol filter 118 pre-screens the air. A series of UV lamps 98 are disposed opposite a catalyst-coated liner or surface 100.

Again, the fan speed is controlled by the microprocessor via motor 64 which receives the input from detector 44. Humidity is adjusted in the same manner as described in FIG. 7.

Figure 11:
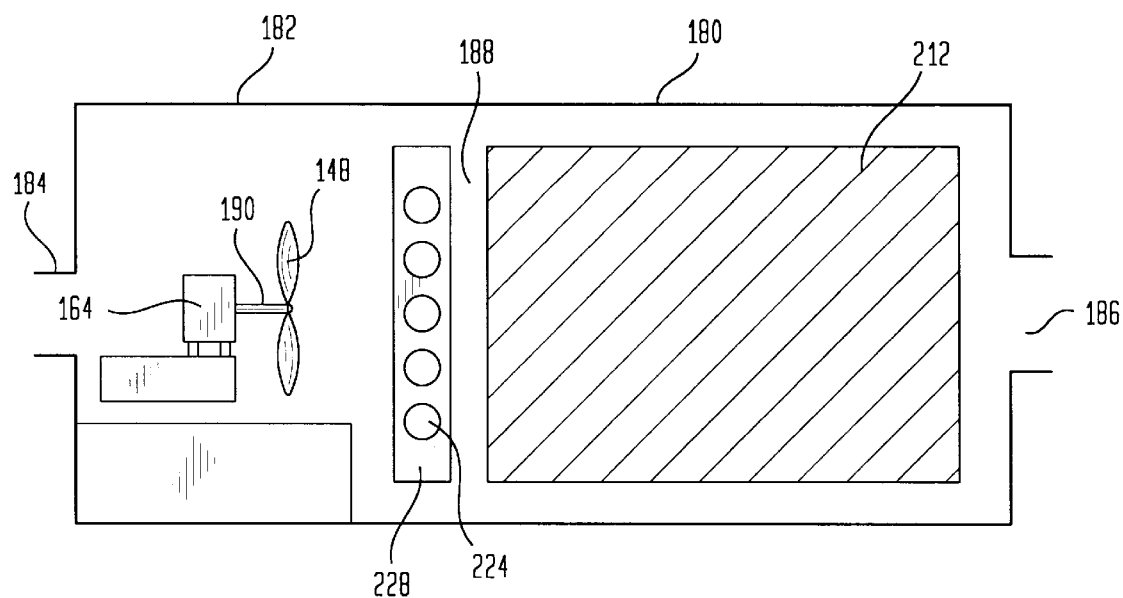
FIG. 11 is a longitudinal cross-sectional view of another stand-alone embodiment in accordance with the present invention.
Figure 12:
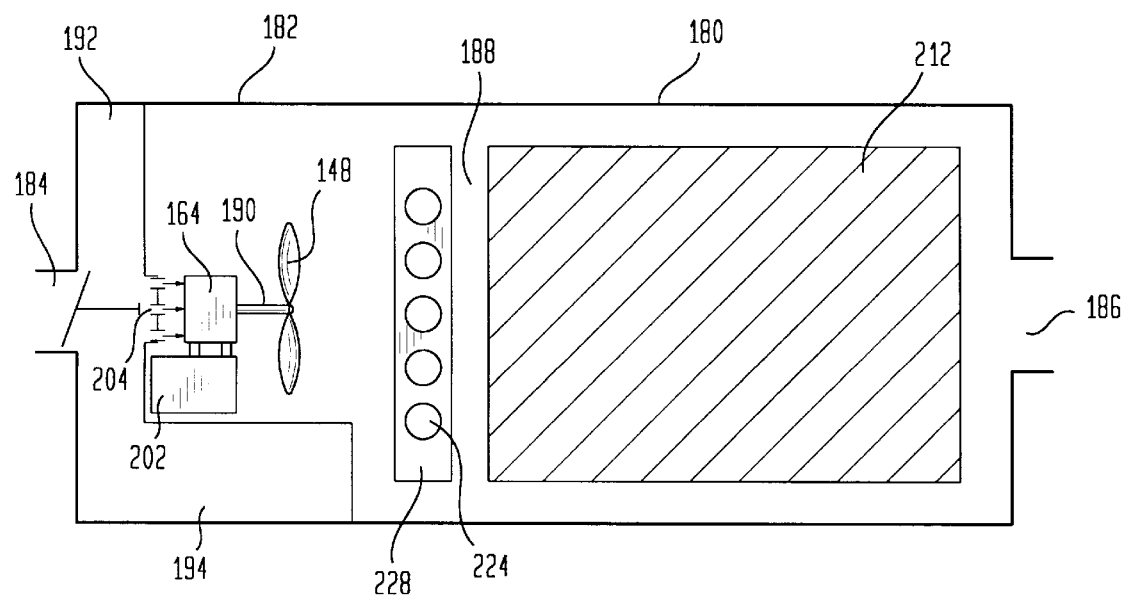
FIG. 12 is a longitudinal cross-sectional view of another stand-alone embodiment in accordance with the present invention.

As shown in FIGS. 11 and 12, the stand-alone units of the present invention may be adapted to receive the reactors of FIGS. 4–6. The base stand-alone unit 180 of FIG. 11 includes a housing 182 having an inlet 184 and outlet 186. Intermediate the inlet and outlet is a chamber 188 that includes a control fan 190 and a fan motor 164 for driving fan 148. The depicted stand-alone units are operated without an air speed detector, and are instead designed and constructed with a constant air flow rate fan adapted to the cross sectional area of the stand unit housing to provide the required residence time for the air flow over the photocatalyst. FIG. 12 depicts a stand-alone unit also containing a humidifier 192 and a dehumidifier 194 with a flow bypass/diverter 204 controlled by microprocessor 202. The microprocessor 202 controls the flow bypass/diverter to direct the inlet air to either the humidifier, dehumidifier or directly into chamber 188, depending upon the humidity of the inlet air as measured by the microprocessor. UV lamp assembly 228 illuminates catalytic insert 212 within chamber 188. FIG. 6 shows the UV lamp assembly 228 of FIGS. 11, 12 and 14, in which a horizontal array of UV lamps 224 are arranged in frame 228 for insertion in the honeycomb structure of FIG. 14.

FIG. 15 depicts a catalytic insert 212 for a reactor in which the insert is illuminated by UV lamp assembly located exterior to the insert. FIG. 14 depicts a reactor 222 in which the UV lamp assembly 228 is located within the catalytic insert 212.

Figure 13:
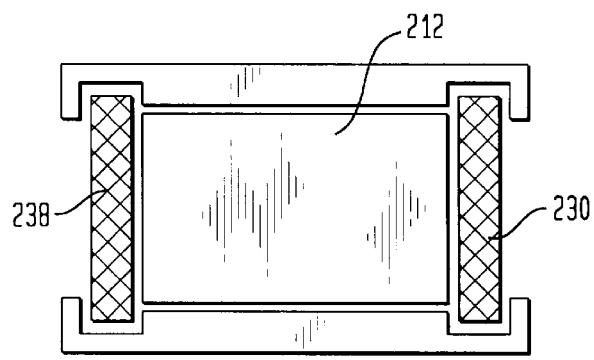
FIG. 13 is a longitudinal cross-sectional view of a catalytic insert in accordance with the present invention.

As noted above, the stand-alone units of FIGS. 11 and 12 are adapted to receive the reactors of FIGS. 4–6. FIG. 13 depicts a reactor specially adapted for use with stand-alone units by containing a prefilter 238 that would otherwise not be suitable for use with most HVAC systems because of the pressure drop that it would produce. The reactor also includes catalytic insert 212 and a photocatalyst-coated after-filter 230. The after-filter may alternatively be coated or impregnated with material like activated carbon or other suitable materials for absorbing VOC's, odors, and the like.

A catalytic insert 212 having a honeycomb structure with square air passages 231 and a built-in lamp assembly 228 is shown in FIG. 14. Such an insert is suitable for use with the stand-alone units of FIGS. 11 and 12. Another suitable catalytic insert for the stand-alone unit of FIGS. 11 and 12 is shown in FIG. 17. Catalytic insert 212 has finned wall passages 226, which serve to increase the catalytic surface area, thus increasing residence time at the same air flow rate and overall space availability. Fins 226 shown in FIG. 17 are rectangular; however, they may be modified in any configuration to control the residence time per unit catalytic area.

Figure 20:
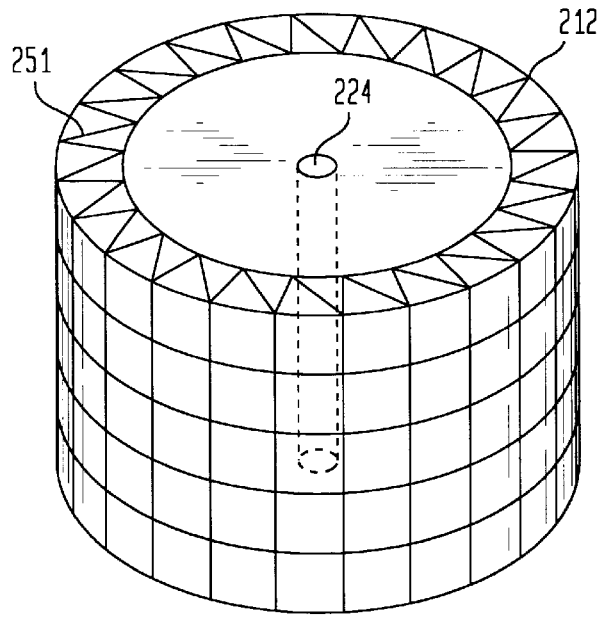
FIGS. 20 and 21 are diagrammatic perspective views of alternative embodiments of reactor units in accordance with the present invention.
Figure 21:
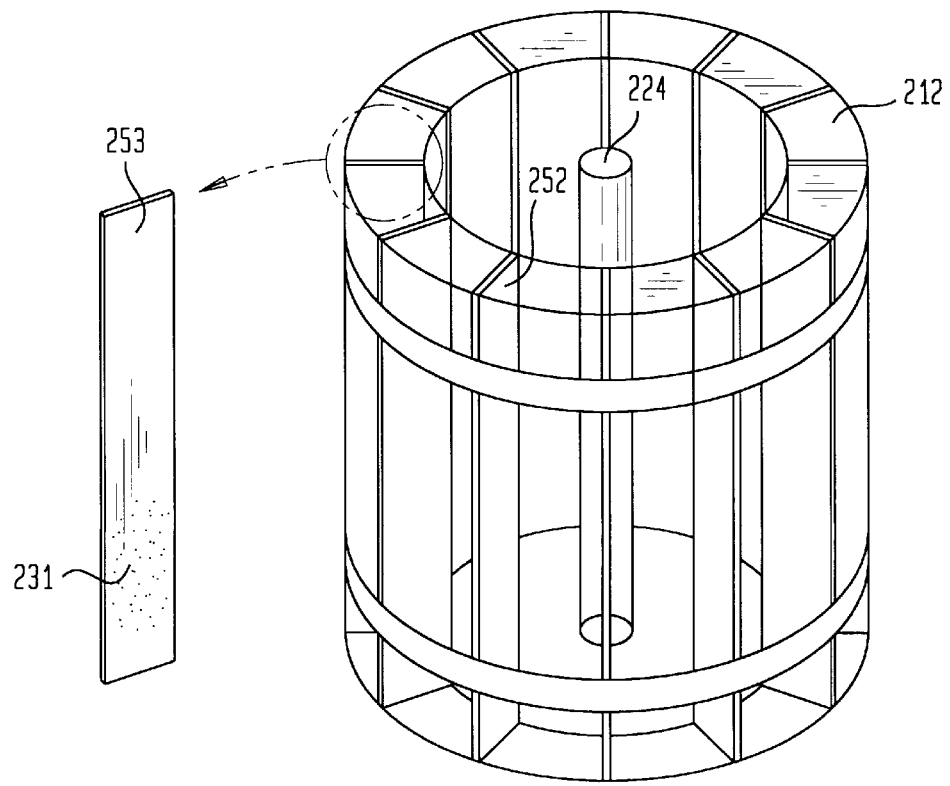

Other catalytic inserts for the stand-alone units of FIGS. 11 and 12 are shown in FIGS. 20 and 21, which depict circular catalytic inserts 212. In FIG. 20, catalytic insert 212 has a pleated surface 251 illuminated from the interior by UV lamp 224. Additional lamps may be fitted at the periphery, or other locations, if required, provided the UV light from the lamps is incident on the catalyst. FIG. 21 depicts a catalytic insert 212 having a flat surface 252 of plastic strips 253 coated with catalyst 231.

FIG. 15 depicts a catalytic insert 212 with a tubular construction having circular or oval air passages 232. The insert contains no UV lamps and is for use with the stand-alone unit of FIG. 11 or 12 in which UV lamp assembly 228 is located in chamber 188 exterior to the photocatalyst-coated insert 212.

The following examples further illustrate the present invention, and are not to be construed as limiting the scope thereof. All parts and percentages are by weight unless expressly indicated to be otherwise, and all temperatures are in degrees Celsius.

EXAMPLES

Materials and Methods

Photolytic and photocatalytic experiments were conducted to determine the effect of catalyzed UV radiation on airborne microorganisms. By trial and error, a correct dilution of *Serratia marcescens* was found which gave appropriate counts on agar plates. 20 milliliters of the diluted Serratia culture was transferred into a nebulizer which was operated by 99.999% pure compressed nitrogen at 30 to 40 psi.

The experimental apparatus consisted of a reactor test section, recirculation duct and a blower. The first four feet of the duct was rectangular in cross-section. This section was attached to nebulizers, one of which contained the diluted Serratia culture, and the other, pure deionized water.

Appropriate air flow through the nebulizer was determined, so that aerosols did not fall to the surface of the duct. Thermocouples and pressure taps were attached to this section to measure the temperature of the air stream before the reactor and the pressure drop across the reactor, respectively.

The second section of the apparatus consisted of the reactor area which housed 24 UV lamps and a Fiberglass filter coated with titanium dioxide and arranged perpendicular to the air flow. This section was 32 inches long, with a cross-sectional area of 400 in$^2$.

The UV lamps used were low pressure mercury lamps (Southern New England RPR-3500A) with an input energy of 14 W. Each lamp emitted approximately 1.5 W of UV-radiation, predominately at 350 nm. The UV light was measured by placing an Eppley radiometer (Model TUVR) perpendicular to the UV lamp at different distances.

Air sampling was conducted at a distance of one foot from the reactor. Four culture plates securely placed on a rack were used to capture viable organisms over a 30 second interval. Thermocouples were attached to this section to measure the temperature.

The recirculating section of the duct consisted of a circular duct with a diameter of one foot. A humidity probe was attached to this section to measure the relative humidity of the air stream. The final part of the apparatus was a blower which was connected to both the circular cross-section duct and the rectangular cross-section duct. The total length of the recirculating test apparatus was 29.5 feet.

The culture plates were prepared using plate count agar, which was selected because it contained seaweed extract with the addition of some nutrients that fulfilled the nutritional requirements for the growth of Serratia bacteria.

Culture plates were prepared by weighing sufficient agar powder on an electronic scale to make a half-liter solution. Agar powder (11.75 grams) was poured into a 500 mL flask of deionized water. The solution was mixed and heated for 10 to 15 minutes with a magnetic stirrer and heater. After the agar powder had completely dissolved, the flask was covered with aluminum foil to prevent airborne contamination, and put into an Autoclave steam sterilizer for 30 minutes for sterilization.

After sterilization, the agar was allowed to cool for ten minutes in a water bath at a temperature of 50° C. The agar was poured into petri dishes using an aseptic technique in a laminar flow hood which was cleaned with isopropyl alcohol prior to use. 500 mL of agar was poured into the petri dishes, completely covering the bottom of the dish. The dishes were set to gel on the aseptic hood for 24 hours, and then stored upside-down in the refrigerator to prevent the condensate from contacting the agar. The agar plates were used within 48 hours to prevent low level contamination.

The titanium dioxide-coated Fiberglass filter was prepared by coating the TiO$_2$ on a standard 16×25×2 inch Fiberglass air conditioning filter. The TiO$_2$ (Degussa P25) was primarily anatase, with a BET surface area of 50 m$^2$/g and an average particle size of 21 nm.

A thick slurry of TiO$_2$ was made by mixing 50 grams of TiO$_2$ powder and deionized water. The TiO$_2$ solution was mixed well by placing the flask with the thick TiO$_2$ slurry on a magnetic stirrer. Using a foam brush, TiO$_2$ was coated on both sides of the filter. The filter was allowed to dry for six hours, then another coat of TiO$_2$ was applied on the filter. After the filter was completely dry and the TiO$_2$ was sufficiently affixed, it was placed in the recirculating duct. Operation of the reactor with the TiO$_2$-coated filter in place is denoted as Configuration A.

Several experiments were performed utilizing a coated surface reactor configuration (Configuration B) instead of the Fiberglass filter configuration (Configuration A). The coated surface reactor was used to increase the area for the reaction. The area which was coated with $TiO_2$ was approximately 720 in$^2$. The duct was coated by preparing the $TiO_2$ slurry described above and using a foam brush to coat the surface of the duct with the $TiO_2$ slurry. A heat gun was used to dry the surface. After 8 hours, the surface was coated again, and dried with a heat gun.

Relative humidity and UV intensity parameters were investigated to determine the optimum conditions for the destruction of bacteria. The humidity was varied from 30% RH to 85% RH, and the UV intensity was varied from 20 W/m$^2$ to 100 W/m$^2$.

In the humidity experiments, the air was humidified by atomizing deionized water into the duct. The air flow inside the duct was kept constant at 74 ft/min, and the UV was kept constant at 100 W/m$^2$. A humidity probe (Mamac Humidity Sensor) was attached to the duct to monitor the relative humidity (RH) of the air stream inside the duct. A silica based desiccant material was placed inside the duct to lower the humidity when needed.

The blower was turned on and allowed to stabilize for 10 to 20 minutes before the culture was atomized. All of the liquid bacterial culture in the nebulizer was allowed to completely atomize and stabilize before the initial sample was taken. After the initial sample was taken, the UV lamps were turned on and initial temperature and humidity data were recorded. Four samples were collected on agar plates at predetermined time intervals. The agar plates were exposed to the contaminated air stream for 30 seconds for collection of bacteria. Samples collected during the time intervals were kept in a relatively sterile environment to avoid contamination for the duration of the experiment. After the completion of the experiments, samples were placed upside-down in an incubator at a temperature of 30° C. for 24 hours of incubation. After 24 hours of incubation, the bacterial colonies were quantified on a colony counter having a magnified lens and grid lines which facilitated an accurate count of bacterial colonies.

After the experiment was completed, the duct was cleaned to avoid contamination. Formaldehyde solution was atomized by the nebulizer into the system to decontaminate the duct. The blower was allowed to run in an air-tight duct for two hours. After this process, the top of the duct was left open to outside air for 12 hours before starting the next set of experiments.

Example 1

Effect of Relative Humidity

Both photolysis (UV only, no $TiO_2$) and photocatalysis experiments were performed at relative humidities of 30%, 50% and 85%. FIGS. 24–26 depict the destruction of Serratia by photolysis and photocatalysis at 30% RH, 50% RH and 85% RH, respectively. At 30% RH, no significant difference was observed between photolysis and photocatalysis and complete destruction of the microorganisms was not achieved. This may be attributable to insufficient $H_2O$ to transfer the necessary hydroxyl radicals or superoxides to the bacterium. At 30% RH, it can be inferred that most of the bacterial destruction was attributable to the UV photons attacking the bacteria (photolysis). At 50% RH, the destruction rate for the first three hours was the same for both photolysis and photocatalysis; but after three hours, the destruction rate for photocatalysis was much greater as a result of which 100% inactivation of bacteria was achieved in about 13 hours.

RH was further increased to 85% to determine if a further increase in water vapor would increase the destruction rate. However, higher RH did not increase the destruction of the bacteria. One possible explanation is that the high humidity may induce reactivation of organisms. A comparison of photocatalysis effectiveness for 30%, 50% and 85% RH is shown in FIG. 27. The numerical values for bacteria destruction are set forth in the Table below:

Estimated Lethal Doses At Various Humidities

| RH | $LD_{50}$ W · min/$m^2$ | $LD_{75}$ W · min/$m^2$ | $LD_{100}$ W · min/$m^2$ |
|---|---|---|---|
| PHOTOLYSIS EXPERIMENTS | | | |
| 30% | 1660 | 3320 | — |
| 50% | 1470 | 3870 | — |
| 85% | 1900 | 5010 | — |
| PHOTOCATALYSIS EXPERIMENTS WITH CONFIGURATION A | | | |
| 30% | 1643 | 3310 | — |
| 50% | 1210 | 2178 | 6092 |
| 85% | 1107 | 1660 | — |
| PHOTOCATALYSIS EXPERIMENTS WITH CONFIGURATION B | | | |
| 30% | 2215 | 5530 | — |
| 50% | 870 | 1190 | 876 |

Notes:
1. Dose = UV Intensity · Time
2. Dashed line signifies that destruction did not occur.

As reflected in the above table, the humidity experiments were repeated with Configuration B. Because a greater photocatalysis surface area was present in this configuration, lower dosages of UV energy were needed to attain the indicated levels of destruction.

100% bacteria destruction was not obtained using photolysis alone, regardless of the RH level. In both Configuration A and Configuration B, 100% bacteria destruction was only obtained at an RH level of 50%. 100% destruction was not obtained at 30% or 85% RH for Configuration A or for 30% RH for Configuration B. A comparison of Configuration A to Configuration B and photolysis (UV only) at 50% RH is shown in FIG. 28.

Example 2

Effect of UV Intensity

Photocatalysis experiments were performed at the aforementioned intensity levels. The RH was kept at 50% and air flow rate at 74 ft/min. The results are depicted in FIG. 29.

It is evident from these results that higher UV intensity results in higher destruction rates. After 8 hours of radiation, the photocatalytic destruction rates for 100 $W/m^2$ started to level off. For lower intensities, the destruction was actually increasing after 6 hours of exposure. This probably indicated that the bacteria weakened after irradiation and became vulnerable to photons and hydroxyl radical attack after 6 hours even at lower radiation levels.

Titanium dioxide in the presence of UV radiation thus enhances the destruction rate of microorganisms, with complete destruction occurring at 50% RH. At low RH (30%), titanium dioxide did not accelerate the bacterial destruction. At higher RH (85%), 10% of the organisms were still viable.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. All such modifications are intended to be included within the scope of the following claims.

What is claimed is:

1. A method for disinfecting an air stream containing microorganisms, comprising:
   providing an air stream containing microorganisms having a relative humidity greater than about 40%; and
   contacting said air stream with a photocatalyst having a predetermined band gap energy in the presence of a source of photons having a wavelength corresponding to said band gap energy of said photocatalyst, so that at least a portion of said microorganisms in said air stream are destroyed by photocatalytic oxidation.

2. The method of claim 1, wherein said microorganisms are completely destroyed.

3. The method of claim 1, further comprising the step of controlling the flow rate of said air stream so that said microorganisms are completely destroyed.

4. The method of claim 1, wherein said relative humidity is between about 40 and about 70%.

5. The method of claim 4, wherein said relative humidity is between about 50 and about 60%.

6. The method of claim 5, wherein said relative humidity is about 50%.

7. The method of claim 1, wherein said photocatalyst is a semiconductor.

8. The method of claim 7, wherein said semiconductor is $TiO_2$.

9. The method of claim 1, wherein said source of photons comprises UV light.

10. The method of claim 9, wherein said UV light has a wavelength between about 300 and about 400 nm.

11. The method of claim 1, wherein said photocatalyst is coated on the surface of an open filter medium.

12. The method of claim 11, wherein said filter medium is disposed transverse to the flow of said air stream.

13. The method of claim 11, wherein said filter medium is capable of trapping bioaerosols.

14. A device for disinfecting a quantity of air containing microorganisms, comprising:

a surface coated with a photocatalyst having a predetermined band gap energy;

means for illuminating said photocatalyst-coated surface with a source of photons having a wavelength corresponding to said band gap energy of said photocatalyst;

means for contacting said air with said photocatalyst-coated surface; and means for maintaining the relative humidity of said air above about 40%, so that at least a portion of said microorganisms in said air are destroyed by photocatalytic oxidation upon contact with said photocatalyst when said photocatalyst-coated surface is illuminated with said source of photons.

15. The device of claim 14, further comprising means for controlling the flow rate of said air, so that the residence time of said air with said photocatalyst is effective for complete destruction of said microorganisms in said air.

16. The device of claim 14, wherein said photocatalyst is a semiconductor.

17. The device of claim 16, wherein said semiconductor is $TiO_2$.

18. The device of claim 14, wherein said photocatalyst-coated surface comprises an open filter medium coated with said photocatalyst and disposed transverse to the flow of said air.

19. The device of claim 18, wherein said filter medium is capable of trapping bioaerosols.

20. The device of claim 19, comprising a HEPA filter containing said photocatalyst-coated filter medium.

21. The device of claim 19, comprising a microporous filter containing said filter medium.

22. The device of claim 14, wherein said source of photons comprises UV light.

23. The device of claim 22, wherein said UV light has a wavelength between about 300 and about 400 nm.

24. A device for disinfecting air containing microorganisms comprising:

a duct through which said air is moved;

a blower connected to said duct to move said air therethrough;

a photocatalyst having a predetermined band gap energy disposed in said duct;

a lamp disposed in sufficient proximity to said photocatalyst to illuminate said photocatalyst with a source of photons having a wavelength corresponding to said band gap energy of said photocatalyst; and a humidity controller adapted to regulate the relative humidity of said air in said duct above about 40%, so that at least a portion of said microorganisms in said air are destroyed by photocatalytic oxidation upon contact with said photocatalyst when said photocatalyst is illuminated with said source of photons from said lamp.

25. The device of claim 24, wherein said humidity controller is adapted to regulate the relative humidity of said air in said duct within a range effective to completely destroy said microorganisms.

26. The device of claim 24, wherein said humidity controller is adapted to maintain the relative humidity of said air in said duct between about 40% and about 70%.

27. The device of claim 24, wherein said photocatalyst is a semiconductor.

28. The device of claim 27, wherein said semiconductor is $TiO_2$.

29. The device of claim 24, wherein said photocatalyst is coated on a filter medium positioned transverse to the flow of said air in said duct.

30. The device of claim 29, wherein said filter medium is capable of trapping bioaerosols.

31. The device of claim 30, comprising a HEPA filter containing said photocatalyst-coated filter medium.

32. The device of claim 30, comprising a microporous filter containing said photocatalyst-coated filter medium.

33. The device of claim 24, wherein said photocatalyst is coated on at least one interior wall of said duct.

34. The device of claim 24, wherein said photocatalyst is coated on at least one interior wall of a liner inserted in said duct.

35. The device of claim 34, wherein at least one inside wall of said duct liner has fins affixed to the surface thereof coated with said photocatalyst, thereby increasing the photocatalyst-coated surface area of said duct liner.

36. The device of claim 24, wherein said source of photons comprises UV light.

37. The device of claim 36, wherein said UV light has a wavelength between about 300 and about 400 nm.

38. The device of claim 24, further including a humidity detector disposed in said duct.

39. The device of claim 38, further including a microprocessor adapted to control said humidity controller based on information received from said humidity detector.

40. The device of claim 39, further including an air speed detector disposed in said duct, wherein said microprocessor is further adapted to control the speed of said blower based on information received from said air speed detector.

41. The device of claim 24, further including an air speed detector disposed in said duct.

42. The device of claim 41, further including a microprocessor adapted to control the speed of said blower based on information received from said air speed detector.

43. The device of claim 42, further including a humidity probe disposed in said duct, wherein said microprocessor is further adapted to control said humidity controller based on information received from said humidity probe.

44. The device of claim 24, further including a microprocessor adapted to control said humidity controller.

45. The device of claim 24, further including a microprocessor adapted to control the speed of said blower.

46. The device of claim 24, wherein said duct is part of a heating, ventilation and air conditioning system.

47. The device of claim 46, wherein said blower is part of a heating, ventilation and air conditioning system.

48. The device of claim 46, wherein said humidity controller is part of a heating, ventilating and air conditioning system.

49. The device of claim 24, further including a filter medium downstream of said photocatalyst in contact with said air moving through said duct.

50. The device of claim 49, wherein said filter medium downstream of said photocatalyst is capable of absorbing a material selected from the group consisting of volatile organic contaminants and odors.

51. A device for disinfecting air containing microorganisms comprising:
   a photocatalyst having a predetermined band gap energy disposed in the air supply register of a heating, ventilating and air conditioning system and a lamp positioned in sufficient proximity to said photocatalyst to illuminate said photocatalyst with a source of photons having a wavelength corresponding to said band gap energy of said photocatalyst;
   wherein said heating, ventilating and air conditioning system has a blower to move air through said air supply register and a humidity controller adapted to maintain the relative humidity of said air in said heating, ventilating and air conditioning system above about 40%, so that at least a portion of said microorganisms in said air are destroyed by photocatalytic oxidation upon contact with said photocatalyst when said photocatalyst is illuminated with said source of photons.

52. The device of claim 51, wherein said humidity controller is adapted to maintain the relative humidity of said air in said heating, ventilating and air conditioning system between about 40% and about 70%.

53. The device of claim 51, wherein said photocatalyst is a semiconductor.

54. The device of claim 53, wherein said semiconductor is $TiO_2$.

55. The device of claim 51, wherein said photocatalyst is coated on an open filter medium disposed transverse to the flow of said air through said register.

56. The device of claim 55, wherein said filter medium is capable of trapping bioaerosols.

57. The device of claim 56, comprising a HEPA filter containing said filter medium.

58. The device of claim 56, comprising a microporous filter containing said filter medium.

59. The device of claim 51, wherein said photocatalyst is coated on at least one interior surface of a liner inserted in said register.

60. The device of claim 59, wherein said at least one inside surface of said liner has fins affixed to the surface thereof coated with said photocatalyst, thereby increasing the photocatalyst-coated surface area of said liner.

61. The device of claim 51, wherein said source of photons comprises UV light.

62. The device of claim 61, wherein said UV light has a wavelength between about 300 and about 400 nm.

63. The device of claim 51, further including a filter medium downstream of said photocatalyst in contact with said air moving through said duct.

64. The device of claim 63, wherein said filter medium downstream of said photocatalyst is capable of absorbing a material selected from the group consisting of volatile organic contaminants and odors.

65. A stand-alone device for disinfecting air containing microorganisms comprising:
   a chamber through which said air is moved;
   a blower connected to said chamber to move said air therethrough;
   a photocatalyst having a predetermined band gap energy disposed in said chamber;
   a lamp positioned to illuminate said photocatalyst with a source of photons having a wavelength corresponding to said band gap energy of said photocatalyst; and
   a humidity controller adapted to maintain the relative humidity of said air in said chamber above about 40%, so that at least a portion of said microorganisms in said air are destroyed by photocatalytic oxidation upon contact with said photocatalyst when said photocatalyst is illuminated with said source of photons.

66. The device of claim 65, wherein said humidity controller is adapted to maintain the relative humidity of said air in said chamber above about 40%.

67. The device of claim 65, wherein said photocatalyst is a semiconductor.

68. The device of claim 67, wherein said semiconductor is $TiO_2$.

69. The device of claim 65, wherein said photocatalyst is coated on an open filter medium disposed transverse to the flow of said air through said chamber.

70. The device of claim 69, wherein said filter medium is capable of trapping bioaerosols.

71. The device of claim 70, comprising a HEPA filter containing said filter medium.

72. The device of claim 70, comprising a microporous filter containing said filter medium.

73. The device of claim 65, wherein said photocatalyst is coated on at least one interior surface of said chamber.

74. The device of claim 65, wherein said photocatalyst is coated on at least one interior surface of a liner inserted in said chamber.

75. The device of claim 74, wherein said at least one inside surface of said liner has fins affixed to the surface thereof coated with said photocatalyst, thereby increasing the photocatalyst-coated surface area of said liner.

76. The device of claim 65, wherein said source of photons comprises UV light.

77. The device of claim 76, wherein said UV light has a wavelength between about 300 and about 400 nm.

78. The device of claim 65, further including an air speed detector disposed in said chamber.

79. The device of claim 78, further including a microprocessor adapted to control the speed of said blower based on information received from said air speed detector.

80. The device of claim 79, further including a humidity probe disposed in said chamber, wherein said microprocessor is further adapted to control said humidity controller based on information received from said humidity probe.

81. The device of claim 65, further including a humidity probe disposed in said chamber.

82. The device of claim 81, further including a microprocessor adapted to control said humidity controller based on information received from said humidity probe.

83. The device of claim 65, further including a microprocessor adapted to control said humidity controller.

84. The device of claim 65, further including a microprocessor adapted to control the speed of said blower.

85. The device of claim 65, further comprising a particulate prefilter through which said air is moved prior to entering said chamber.

86. The device of claim 85, wherein said particulate prefilter comprises a filter medium capable of trapping bioaerosols.

87. The device of claim 86, wherein said prefilter is a HEPA filter.

88. The device of claim 86, wherein said prefilter is an electrostatic filter.

89. The device of claim 86, wherein said prefilter is a microporous filter.

90. The device of claim 65, further including a filter medium downstream of said photocatalyst in contact with said air moving through said chamber.

91. The device of claim 90, wherein said filter medium downstream of said photocatalyst is capable of absorbing a material selected from the group consisting of volatile organic contaminants and odors.

* * * * *